United States Patent
Ali et al.

(10) Patent No.: US 6,501,818 B1
(45) Date of Patent: Dec. 31, 2002

(54) APPARATUS AND METHODS FOR DISPLAYING COMPUTED TOMOGRAPHY FLUOROSCOPY IMAGES INCLUDING DATA TRANSFER PROVIDED OVER A NETWORK

(75) Inventors: Fazle Ali, Brookfield, WI (US); Jiang Hsieh, Waukesha, WI (US); Girish Saligram, Brookfield, WI (US); Shawn Patrick Faessler, Milwaukee, WI (US); Christopher Joseph Mussack, Waukesha, WI (US); David Matthew Deaven, Waukesha, WI (US); Aleksandar Zavaljevski, Waukesha, WI (US); Stanley Fox, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/473,929

(22) Filed: Dec. 28, 1999

Related U.S. Application Data (63) Continuation-in-part of application No. 08/978,803, filed on Nov. 26, 1997.

(51) Int. Cl.$^7$ .................................................. A61B 6/03
(52) U.S. Cl. .......................................... 378/4; 378/901
(58) Field of Search ........................... 378/4, 8, 15, 901

(56) References Cited

U.S. PATENT DOCUMENTS

| | | |
|---|---|---|
| 5,371,778 A | 12/1994 | Yanof et al. |
| 5,708,690 A | 1/1998 | Hsieh ............................. 378/4 |
| 6,400,790 B1 * | 6/2002 | Ohnesorge et al. ........... 378/15 |
| 6,411,670 B1 * | 6/2002 | Besson ........................... 378/4 |

* cited by examiner

*Primary Examiner*—David V. Bruce
(74) *Attorney, Agent, or Firm*—Foley & Lardner; Peter J. Vogel; Michael A. Della Penna (57) ABSTRACT

A computed tomography system includes an x-ray source, an x-ray detector aligned with the x-ray source, a processor coupled to the x-ray detector, and a display for displaying reconstructed images. The processor is programmed to perform at least one of: generating a partially reconstructed image for display on the display; dynamically reformatting images for display on the display; communicating the partially reconstructed image, the reformatted images, or data associated with the system to a remote facility.

22 Claims, 6 Drawing Sheets

APPARATUS AND METHODS FOR DISPLAYING COMPUTED TOMOGRAPHY FLUOROSCOPY IMAGES INCLUDING DATA TRANSFER PROVIDED OVER A NETWORK

CROSS REFERENCE TO RELATED APPLICATIONS

This application is a continuation-in-part (CIP) of U.S. patent application Ser. No. 08/978,803, entitled "Apparatus And Methods For Displaying Computed Tomography Fluoroscopy Images" by Fazle Ali et al. filed on Nov. 26, 1997.

BACKGROUND OF THE INVENTION

The present invention relates generally to the field of medical diagnostic systems, such as imaging systems. More particularly, the invention relates to an apparatus and technique for enhancing the display of images during CT fluoroscopy scans.

In at least one known CT system configuration, an x-ray source projects a fan-shaped beam which is collimated to lie within an X-Y plane of a Cartesian coordinate system, generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reduced scanning time, helical scanning provides other advantages such as better control of contrast, improved image reconstruction at arbitrary locations, and better three-dimensional images.

In CT fluoroscopic systems ("CT Fluoro"), sequential frames of images are generated to help, for example, in guiding a needle to a desired location within a patient. A frame, like a view, corresponds to a two dimensional slice taken through the imaged object. Particularly, projection data is processed at a high frame rate to construct an image frame of the object.

With known CT Fluoro systems, the general objective is to provide the physician with as much useful information as quickly as possible to guide the procedure. For example, one important parameter in CT Fluoro systems in the "time to first image", i.e., the lag time between x-ray turned on and the first frame. Reducing the time to the first image provides the operator with a better sense of the situation. In addition, the information should be displayed and retrievable in a format definable by the physician.

It would be desirable to improve CT support for interventional procedures. Particularly, it would be desirable to acquire data, reconstruct such data and display an image for such data quickly enough to guide an interventional procedure. It also would be desirable to improve the image display for interventional procedures.

Solutions to the problems described above have not heretofore included significant remote capabilities. Thus, there is a need for a medical diagnostic system which provides for the advantages of remote services and addresses the problems described above. In particular, there is a need for remote upgrades, remote diagnostics, remote servicing, remote viewing, remote file storage, remote control, and remote adjustments to the reformatting and reconstruction methods, parameters, or functions. Furthermore, there is a need for contractual arrangements, such as, per use licenses which lease the medical diagnostic equipment based on use. Additionally, remote services include expert on-line assistance for image scanning techniques, image analysis, pathology detection, imaging unit maintenance, and other expert-aided operations.

BRIEF SUMMARY OF THE INVENTION

One embodiment of the invention relates to a computed tomography system including an x-ray source, an x-ray detector aligned with said x-ray source, a processor coupled to said x-ray detector, and a display for displaying reconstructed images. The processor is programmed to perform at least one of: generating a partially reconstructed image for display on said display; dynamically reformatting images for display on said display; and communicating the partially reconstructed image, the reformatted images, or data associated with the system to a remote facility. The remote facility provides remote services.

Another embodiment of the invention relates to a computed tomography system including an x-ray source, an x-ray detector aligned with said x-ray source, a processor coupled to said x-ray detector, and a display for displaying reconstructed images. The processor is configured to generate a partially reconstructed image for display on said display, to weight data to provide a smooth transition from a first image to a next image, and to communicate the partially reconstructed image or data associated with the system to a remote facility. The remote facility provides remote services.

Another embodiment of the invention relates to a computed tomography system including an x-ray source, an x-ray detector aligned with said x-ray source, a processor coupled to said x-ray detector, and a display for displaying reconstructed images. The processor is configured to dynamically reformat images for display on said display and to communicate the reformatted images or data associated with the system to a remote facility. The remote facility provides remote services.

Other principle features and advantages of the present invention will become apparent to those skilled in the art upon review of the following drawings, the detailed description, and the appended claims.

BRIEF DESCRIPTION OF THE DRAWINGS

Preferred exemplary embodiments are described below with reference to the accompanying drawings, wherein like reference numerals denote like elements.

DETAILED DESCRIPTION OF THE PREFERRED EMBODIMENT

Figure 1:
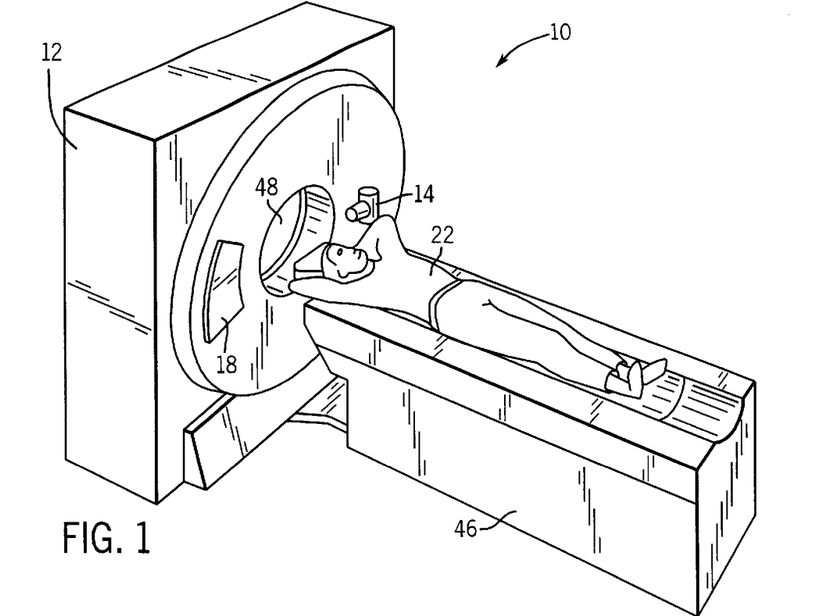
FIG. 1 is a pictorial view of a CT imaging system.
Figure 2:
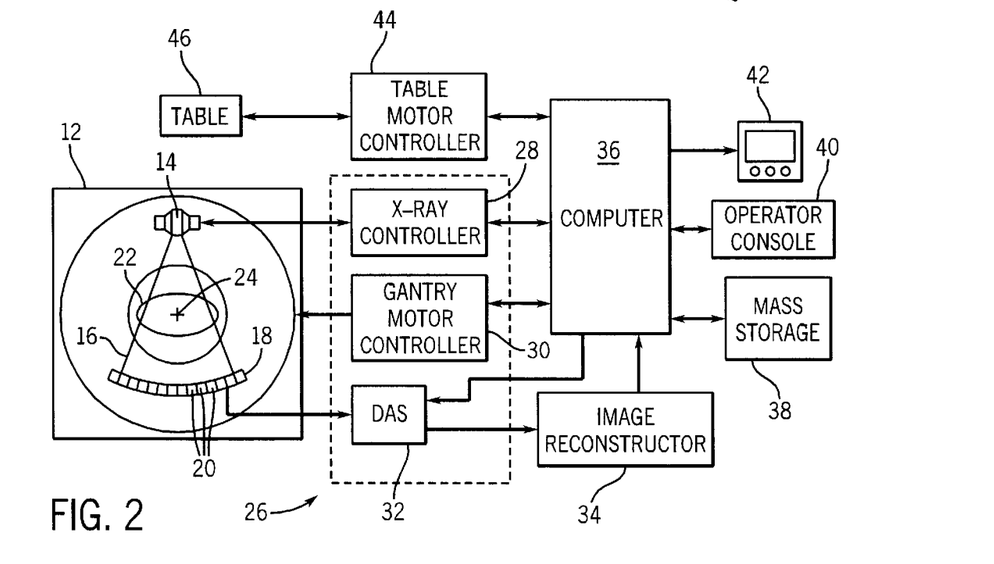
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. The present invention is not limited to practice in connection with third generation scanners and can be used, for example, in fourth generation scanners and in CT electron beam type scanners. Therefore, although the present invention is sometimes described herein in connection with third generation scanners, it should be understood that such description is by way of example only, and not by way of limitation.

With respect to system 10, gantry 12 has an x-ray source 14 that projects a beam of x-rays 16 through a source collimator (not shown) and at a gantry angle (not shown) toward a detector array 18 on the opposite side of gantry 12. Detector array 18 is formed by detector elements 10 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38. Preferably, the reconstructed image is stored as a data array.

Computer 36 also receives commands and scanning parameters from an operator via console 40 that has a keyboard. An associated display 42, such as a flat panel or a cathode ray tube display, allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. As used herein, an Xmm by Xmm scan refers to scanning an object of interest using an X mm collimator aperture at a 1:1 helical pitch, wherein helical pitch is the ratio of table 46 movement in one rotation of the x-ray source 14 to the slice width defined by the source collimator.

The following description sets forth details regarding various display apparatus and methods that can be practiced in CT Fluoro and other applications to provide operators with enhanced display options. The apparatus and methods are referred to below as partial image display, dynamic image reformation, in-room control, flat panel display, and in-room display. Each of these apparatus and methods can be practiced by themselves in a CT Fluoro System, or in any combination, to provide the desired operational results.

A. Partial Image Display

As explained above, an important performance parameter for a CT Fluoro System is the time to first image. By generating a first image more quickly, the operator is provided with more information and should have a better sense of control since timely feedback is provided. Accordingly, and to reduce the time to first image, a partially reconstructed image can be displayed. For example, a set of images can be produced using 1/6 to 5/6 of the full views and overscan weights. The views can be displayed at roughly a rate of 6 frames per second. In one specific system, the partially reconstructed images can be displayed when 120, 232, 352, 464, and 584 views are accumulated in the first image generation memory buffer. The overscan algorithm may, for example, be the overscan algorithm described in copending U.S. patent application Ser. No. (15-CT-4313), entitled Image Reconstruction In A Computed Tomography Fluoroscopy System, which is assigned to the present assignee and incorporated herein, in its entirety, by reference. The overscan angle may, for example, be 22.0 degrees.

Generally, the partially reconstructed image is obtained with the weighting scheme. Since most of the motion artifact suppression weights (e.g., overscan weights) suppress the contribution from the start of the scan and gradually increase the contribution of the views to the final image, overscan weighting presents a smoother transition from image to image as the partially reconstructed images are displayed, as compared to no weights. Of course, other weighting schemes can be used.

B. Dynamic Image Reformation

Examining the needle position from different orientations, i.e., views, sometimes is desired. To address this need, dynamic image reformation can be performed. Particularly, axial images are displayed at a very high rate and the operator may reformat the axial images and display the reformatted images in real time. The operator may therefore view the needle from different angles and obtain depth information.

The image reformation may be performed by image interpolation. Particularly, image reformation refers to viewing a cut-through plane of an object. That is, in a conventional CT display, a series of images perpendicular to the z-axis are generated and displayed. If the same object is desired to be viewed along a plane that is in alignment with the z-axis which forms a 45 degree angle with the x-y axis, then the intersection of this new plane with the set of planes that represent the CT image is determined. Once the intersections are determined, a reformatted image can be formed by linear interpolation of the original CT images along the intersections. Image reformation algorithms are known.

C. In-room Control

To provide additional functionality and convenience for a user, the following functions can be provided by an in-room control, or convenient, hand held unit. The manner in which commands are communicated from the remote unit to the display are well known in the art. The functions are generally referred to as "reverse and forward", "save" (or capture), "grid display", and "preset window/levels". By enabling an operator to perform these functions with the remote unit, the system is believed to be easier to use and useful information to the operator in an easily understandable format.

The "reverse and forward" function is a double functionality control with a deadman control (push and hold button) and a momentary or single push button. Specifically, when the button is pushed and released as a momentary function, a command to advance or reverse (depending on which button is pushed) one image for each button press is communicated to the display. When the button is pushed and held for more than a pre-defined time, e.g., two seconds, a command to display images in real time, e.g., 6 images per second, forward or backward (depending on the button pressed) will be communicated to the display. The images are stored in a memory buffer (e.g., the last 120 images are stored in the buffer) to enable such function. When the button is released, the play function stops.

The "save" function is a momentary or single push button on the remote unit, and by depressing the save button, a command is transmitted to the display so that the image then displayed on the screen will be captured or saved to the display memory buffer or database. The captured images can be recalled for display, analysis, filming, archiving, and networking.

The "grid display" function is a momentary or single push button. When the grid display button is depressed, a command is transmitted to the display so that a grid pattern scaled in square centimeters is superimposed over the image. Consecutive button pushes activate and deactivate the grid display.

The "preset window/levels" function is a momentary or signal push button. Each time the preset window/levels button is depressed, a command is transmitted to the display to advance one predefined window/level setting. Alternatively, it is contemplated that one button push can cause the window/level setting to change in accordance with preprogrammed or defined settings selected by the operator. It is believe that the by limiting the defined setting to a maximum of 5 to avoid confusion. The setting name and/or values are displayed on the display screen with the image, and the command causes the display to sequence through window/level parameter settings in a continuous loop, advancing one setting with each push of the button. Sequencing typically occurs only in one ordered direction.

Although a hand held unit is described above, the in-room control could be provided by voice activated command device, or the controls can be provided by touching an LED, or hand gestures could be used in combination with a remote sensing device. Therefore, it should be understood that the foregoing description of an in-room control is not limited to practice with a hand held device.

Generally, the functionality that is controllable by a remote control includes, but is not limited to, forward and reverse image review in either fast or slow speed, image save, grid display, and selection of a pre-set of window/level settings. The grid display could be a grid, concentric circles (polar coordinates) at the target, or a ruler along the trajectory of the needle path, or a combination of these displays.

D. Flat Panel Display

To provide improved display, a flat panel display may be utilized. Such displays are commercially available, and one display suitable for use in CT Fluoro systems in Model No. ATC1245B of Allus Technology Corp., 12611 Jones Road, Houston, Tex., 77070. The display, in one embodiment has a 1280×1024 pixel configuration, good image resolution, and has about a 15"–17" diagonal size. The display may, of course, be smaller or larger.

The display is ceiling suspended. Such ceiling suspension system are commercially available, and one suspension system suitable for use in CT Fluoro systems is Model No. 6262 of Mavig, 202 Whistle Stop, Pittsford, N.Y., 14534. The suspension system is located at the gantry perimeter for access to the display from front/back and right/left sides. The suspension system allows four axis of positionability and can be positioned close in the gantry bore area. The suspension system also is counter poised for easy placement/adjustment by an operator, and can be moved quickly for access to a patient. The display also should have a wide viewing angle to accommodate two viewers and should be a color display to provide an enhanced user interface.

E. In-Room Display

Figure 3:
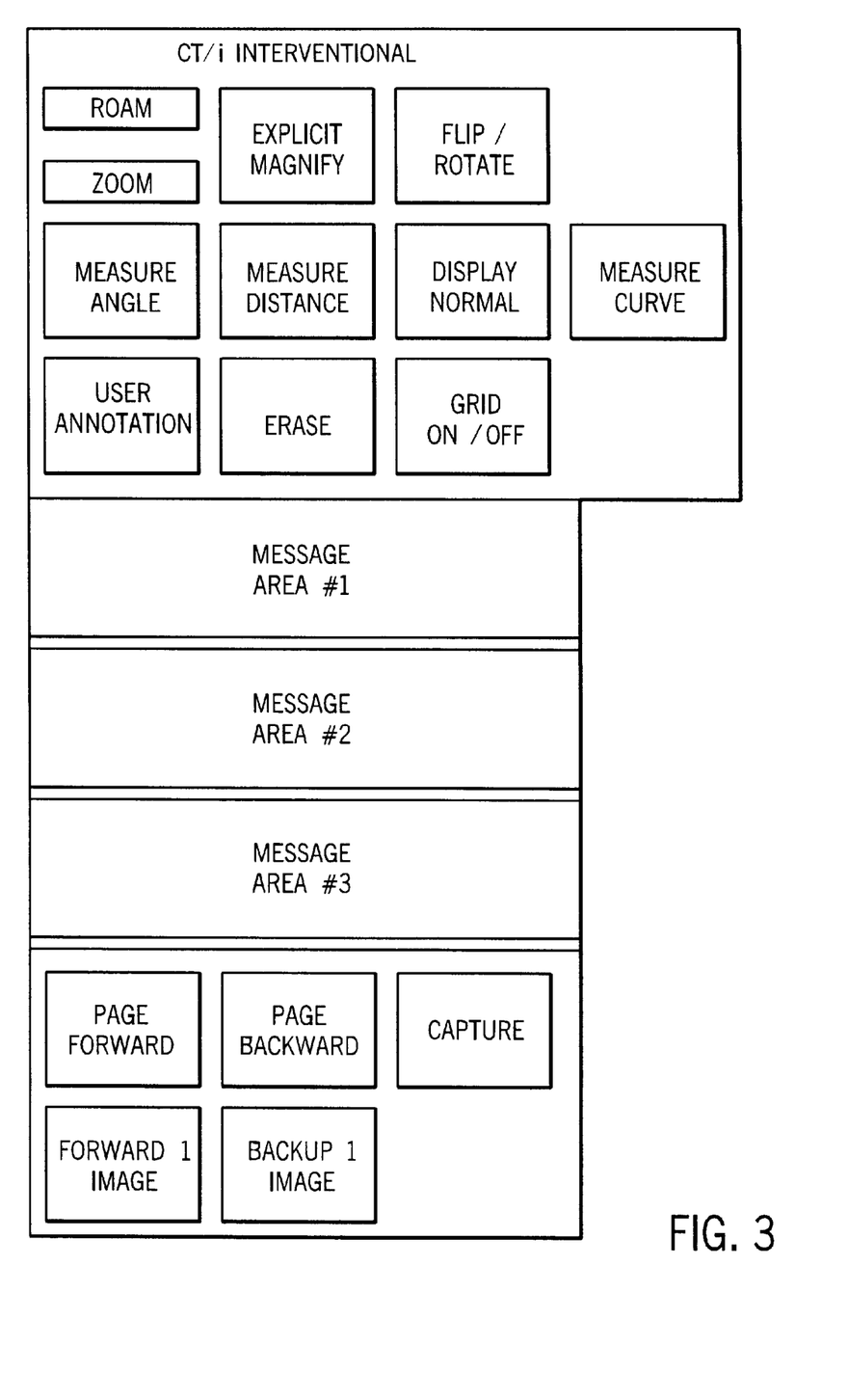
FIG. 3 illustrates a user interface in accordance with one embodiment of the present invention.

A user interface for use with a CT Fluoro system display is illustrated in FIG. 3. Display includes a CT/i Interventional control, three message areas (hierarchical and designated as message area #1, message area #2, and message area #3), and an image control. Interventional control enables the operator to analyze and manipulate images for view on the display. For example, control includes commands for roaming and zooming, for magnifying, and for flipping/rotating an image. Control also includes commands for measuring an angle, distance, and curve. A control command also is provided to return the display to the normal display mode of operation.

Control further includes a command to allow user annotations to be added to an image, and a command to erase annotation. A grid on/off command also is provided which enables a user to have a grid pattern scaled in square centimeters superimposed over the image being displayed.

Messages are displayed in the respective message areas. The most urgent messages are displayed in area #1, less urgent messages are displayed in area #2, and the least urgent messages are displayed in area #3.

Image control includes page forward and page backward commands. The page forward and page backward commands allow the operator to page through the messages displayed in areas #1, #2, and #3 to find the desired message. The forward 1 image and backup 1 image commands enable the operator to select an image for display. The capture command enables an operator to save the image then displayed on the screen to the display memory buffer or database. The captured images can be recalled for display, analysis, filming, archiving, and networking.

The display may also includes two clocks indicating the x-ray exposure time. Particularly, the first clock indicates the exposure during a single run. Whenever the foot switch is initiated, the clock starts to count the number of seconds that the patient is exposed to the x-ray. Specifically, each procedure presently is limited to 90 seconds of exposure, and this first clock helps the operator to better control the patient exposure as well as the timing. The second clock indicates the accumulative exposure time to the patient. For example, during each biopsy operation, multiple x-ray "burst" can be initiated. Between the bursts, the operator will have time to consider the best approach for the next burst. The second clock keeps track of the total amount of exposure performed up to the current time. The clocks serve as indicates that could be either time (length of exposure), total mAs (tube current multiplied by time), or some type of total dose measure to the patient (e.g., organ dose or skin dose) based.

F. Magnification

Real time magnifications of digital images are needed in many applications. Some magnification methods, such as nearest neighbor and bilinear interpolation, are included in general purpose graphic packages and optimized for execution speed on specialized hardware. But higher quality magnification algorithms such as bicubic interpolation are not included. Hence the need arises for methods that approximate bicubic interpolation, but use routines that are accelerated.

As described below in more detail, algorithms for altering the spatial characteristics of digital images can be utilized for such magnification. Generally, one algorithm uses a two pass scheme in which each of the passes represents interpolation in the x and y directions respectively. Bicubic interpolation in each direction is approximated using linear interpolation followed by a one dimensional convolution filter. The other algorithm applies bilinear interpolation first, followed by a two dimensional convolution filter. Note that the order of operation can be reversed. That is, the filtering operation can be applied first followed by the interpolation. The advantage of the reverse order is that the actual area (in terms of mm) covered by the filtering operation is larger. As a result, a smaller filter kernel (e.g., 3×3) covers the same area as a larger kernel in previous case (e.g., 5×5). In addition, before the interpolation, the number of pixels to be filtered is much smaller (256×256 vs. 768×678). The methods can be practiced using the OpenGL graphic package, which is well known in the art. Also, the linear, bilinear, cubic and bicubic interpolations are well known procedures, along With the linear least squares estimation method. By combining linear and bilinear interpolations and digital convolution filters to approximate bicubic interpolation, advantages such as a quickly executable routine are possible. Generally, the algorithms use functions of linear interpolation and digital convolution filters, that are accelerated in OpenGL to approximate the bicubic interpolation. Linear, or bilinear, interpolation is a well defined function. Set forth below are the coefficients of convolution filters to be used in the algorithms.

More particularly, and in the first algorithm, two pass linear interpolation and 1 D filtering is utilized. The first pass performs interpolation in the x direction, and second pass repeats the same procedure for interpolation in the y direction. Interpolations in x and y directions are implemented using identical procedures, and both are performed in two steps. The linear interpolation is performed first, and then the 1 D convolution filter is applied to the interpolated data. The algorithm can be applied for any integer zoom factor n, and for any 1 D convolution filter size m.

To determine the coefficients of the 1 D convolution filter, the following procedure is used. The first step in the procedure is linear interpolation. The values of new pixels $b_i$, with respect to the pixel values of the source image 11, are given by the following equations:

$$Bi = \frac{(n-i=+1)}{n} I_i + \frac{(i-1)}{n} I_2 \quad (1)$$

for i=1, . . . n (n odd), and $$Bi = \frac{(n-i=+0.5)}{n} I_i + \frac{(i-0.5)}{n} I_2 \quad (2)$$

for i=1, . . . n (n even).

Using the linearly interpolated pixels $b_i$, (instances of Bj; i=1, 2, . . . m) the m by 1 convolution filter is applied to obtain the output-pixel $O_k$. Therefore, the following expression for the output pixel $O_k$ is obtained:

$$O_i = \sum_{i=1}^{m} a_i b_i \quad (3)$$

where $a_i$ (i=1, . . . , m) are the coefficients of the convolution filter. When the expressions for $b_i$ (i=1, . . . , m), or the values of corresponding $B_{op}$ from equations (1) or (2), are substituted in equation (3), the following expression is obtained:

$$O_i = \sum_{i_1=1}^{i} \sum_{i_2=1}^{m} K_{i,i_2} a_{i_2} I_{i_1} \quad (4)$$

where $k_{ij}$ are the constant coefficients obtained by applying equations (1) or (2):

Using known expressions for bicubic interpolation, an alternate expression for the pixel value $O_k$ can be obtained:

$$O_k \sum_{i=i}^{4} c_i I_i \quad (5)$$

where $c_i$ are the coefficients derived from the expressions for cubic interpolation in the case of magnification by n. Comparing equations (4) and (5), and equating coefficients with corresponding input pixels values $i_j$, the set of up to four linear equations for the coefficients $a_m$ of the filter is obtained:

$$\sum_{i_2=1}^{m} k_{ii2} a_{i2} = c_i \quad (6)$$

There can be less than four equations if the pixels obtained by bilinear interpolation used by the convolution filter do not have any contribution from some input pixels $i_j$. In that case, the number of equations is reduced by the number of such pixels.

The same procedure is repeated for the set of n consecutive output pixels $O_i$ (i=1, . . . , n) that have different locations relative to the input pixels, and a system of linear equations for the convolution filter coefficients is obtained.

This system can be expressed in matrix form as:

$$C = KA \quad (7)$$

where C is the vector of corresponding coefficients $c_i$ from right sides of equations (6), K is the matrix of coefficients $K_{ij}$ of those linear equations, and A is vector of m filter coefficients $a_i$, (i=1, ..., m). For practical values of zoom factors n and filter sizes m this represents an overdetermined system of linear equations. In this case, the solution is determined by using the linear least squares method, and it has the form:

$$A = (K^T K)^{-1} K^T C \quad (8)$$

Upon determining the coefficients A of the convolution filter that is to be applied, the whole procedure for altering the spatial characteristics of a digital image is defined.

The second algorithm utilizes a two step procedure including bilinear interpolation followed by the application of a 2D convolution filter. The second algorithm can be applied for any integer magnification factor m, and for any 2D convolution filter size n.

As described above, the first step is bilinear interpolation. In the case of magnification by a factor n, there are $n^2$ pixels in the new, zoomed, image that have fundamentally different positions with respect to the pixels of the source image. The values of new pixels, $B_{ij}$, with respect to the pixel values of the source image, $I_{ij}$, are given by following equations:

$$B_{ij} = \frac{(n-i+1)(n-j+1)}{n^2} I_{11} + \quad (9)$$
$$\frac{(n-i+1)(j-1)}{n^2} I_{12} + \frac{(i-1)(n-j+1)}{n^2} I_{21} + \frac{(i-1)(j-1)}{n^2} I_{22}$$

for i,j=1, ..., n (n odd), and $$B_{ij} = \frac{(n-i+0.5)(n-j+0.5)}{n^2} I_{11} + \frac{(n-i+1)(j-0.5)}{n^2} + \quad (10)$$
$$\frac{(i-0.5)(n-j+0.5)}{n^2} I_{21} + \frac{(i-0.5)(j-0.5)}{n^2} I_{22}$$

for i, j=1, ..., n (n even). Values for $b_{ij}$ (instances of $B_{ij}$) can be calculated by using the expressions in equations (9) or (10) and substituting appropriate values for $I_{ij}$, i, and j depending on the position of $b_{ij}$ in the input image.

Using the bilinear interpolated pixels $b_{ij}$ (ij=1, 2, ..., m) the m by m convolution filters applied to obtain the output pixels. The following expression for the output pixel $O_{ki}$ is obtained:

$$O_{ki} = \sum_{i=1}^{m} \sum_{j=1}^{m} a_{ij} b_{ij} \quad (11)$$

where $a_{ij}$ (i,j=1, ..., m) are the coefficients of the convolution filter. If the expressions for $b_{ij}$, (i,j=1, ..., m), or the values of the corresponding $B_{op}$ from equations (9) or (10), are substituted in equation (11), the following expressions are obtained:

$$O_{ki} = \sum_{i_1=1}^{j} \sum_{i_2=1}^{j} \sum_{i_3=1}^{m} \sum_{i_4=1}^{m} k_{i_1 i_2 i_3 i_4} a_{i_3 i_4} I_{i_1 i_2} \quad (12)$$

where a $k_{ijkl}$ are the constant coefficients obtained by applying equations (9) or (10).

Using known expressions for bicubic interpolation, the alternate expression for the pixel value $O_{ki}$ can be obtained:

$$OI = \sum_{i=1}^{4} \sum_{i=j}^{4} c_{ij} I_{ij} \quad (13)$$

where $c_{ij}$ are the coefficients derived from the expressions for bicubic interpolation in the case of magnification by n. Comparing equations (12) and (13), and equating coefficients with corresponding input pixel values Iij, a set of up to sixteen linear equations for the filter coefficients $a_{mn}$, is obtained:

$$\sum_{i_3=1}^{m} \sum_{i_4=1}^{m} k_{iji_3 i_4} a_{i_3 i_4} = c_{ij} \quad (14)$$

There can be less then sixteen equations if the pixels obtained by bilinear interpolation used by the convolution filter do not have any contribution from some input pixels $I_{ij}$. In that case, the number of equations is reduced by the number of such pixels. Repeating this procedure for all of the output pixels $O_{ij}$ (i,j=1, ..., n) a system of linear equations for the convolution filter coefficients is obtained.

This system can be expressed in matrix form as:

$$A = (K^T K)^{-1} K^T C) \quad (15)$$

$$C = KA$$

where C Is the vector of the corresponding coefficients $c_{ij}$ from right sides of equations (14), K is the matrix of coefficients $k_{ijkl}$ of those linear equations, and A is the vector of filter coefficients $a_{ij}$, (i,j=1, ..., m). For practical values of zoom factors n and filter sizes m this represents an overdetermined system of linear equations. In this case, the solution is obtained using the linear least squares method and it has the form:Upon determining the coefficients A of the convolution filter that is to be applied, the whole procedure for altering the spatial characteristics of a digital image is defined.

The above described interface provides the advantage of being easily understood and readily used with minimum training. In addition, the operator is provided with readily accessible information to facilitate performing the procedure.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

Figure 4:
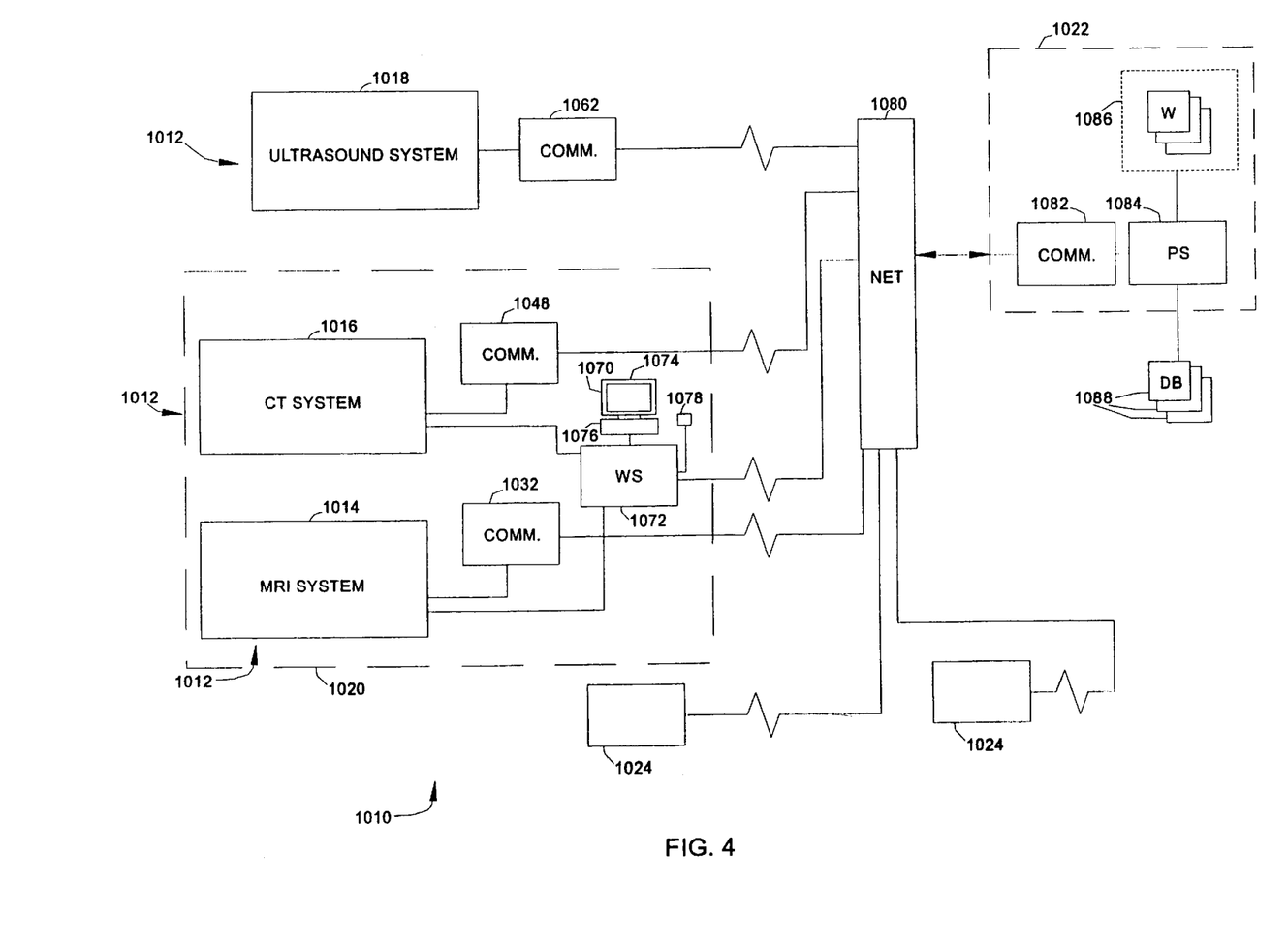
FIG. 4 is a diagrammatical representation of a series of medical diagnostic systems coupled to a service facility via a network connection for providing remote services and data interchange between the diagnostic systems and the service facility.

Referring now to FIG. 4, a service system 1010 is illustrated for providing remote service to a plurality of medical diagnostic systems 1012, including systems such as CT imaging system 10 described with reference to FIG. 1. In the embodiment illustrated in FIG. 4, the medical diagnostic systems include a magnetic resonance imaging (MRI) system 1014, a computed tomography (CT) system 1016, and an ultrasound imaging system 1018. The diagnostic systems may be positioned in a single location or facility, such as a medical facility 1020, or may be remote from one another as shown in the case of ultrasound system 1018. The diagnostic systems are serviced from a centralized service facility 1022. Moreover, a plurality of field service units 1024 may be coupled in the service system for transmitting service requests, verifying service status, transmitting service data and so forth as described more fully below.

In the exemplary embodiment of FIG. 4, several different system modalities are provided with remote service by the service facility. Remote services include but are not limited to services, such as, remote monitoring, remote system control, immediate file access from remote locations, remote file storage and archiving, remote resource pooling, remote recording, and remote high speed computations. Remote services are provided to a particular modality depending upon the capabilities of the service facility, the types of diagnostic systems subscribing to service contracts with the facility, as well as other factors.

Depending upon the modality of the systems, various subcomponents or subsystems will be included. MRI system 1014 includes a uniform platform for interactively exchanging service requests, messages and data with service facility 1022 as described more fully below. MRI system 1014 is linked to a communications module 1032, which may be included in a single or separate physical package from MRI system 1014. In a typical system, additional components may be included in system 1014, such as a printer or photographic system for producing reconstructed images based upon data collected from the scanner.

Similarly, CT system 1016 will typically include a scanner, a signal acquisition unit, and a system controller. The scanner detects portions of x-ray radiation directed through a subject of interest. The controller includes circuitry for commanding operation of the scanner and for processing and reconstructing image data based upon the acquired signals. CT system 1016 is linked to a communications module 1048 for transmitting and receiving data for remote services. Moreover, like MRI system 1014, CT system 1016 will generally include a printer or similar device for outputting reconstructed images based upon data collected by the scanner.

In the case of ultrasound system 1018, such systems will generally include a scanner and data processing unit and a system controller. Ultrasound system 1018 is coupled to a communications module 1062 for transmitting service requests, messages and data between ultrasound system 1018 and service facility 1022.

Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics.

Where more than one medical diagnostic system is provided in a single facility or location, as; indicated in the case of MRI and CT systems 1014 and 1016 in FIG. 4, these may be coupled to a management station 1070, such as in a radiology department of a hospital or clinic. The management station may be linked directly to controllers for the various diagnostic systems. The management system may include a computer workstation or personal computer 1072 coupled to the system controllers in an intranet configuration, in a file sharing configuration, a client/server arrangement, or in any other suitable manner. Moreover, management station 1070 will typically include a monitor 1074 for viewing system operational parameters, analyzing system utilization, and exchanging service requests and data between the facility 1020 and the service facility 1022. Input devices, such as a standard computer keyboard 1076 and mouse 1078, may also be provided to facilitate the user interface.

It should be noted that, alternatively, the management system, or other diagnostic system components, may be "stand-alone" or not coupled directly to a diagnostic system. In such cases, the service platform described herein, and some or all of the service functionality nevertheless be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 1072 and field service units 1024 may be linked to service facility 1022 via a remote access network 1080. For this purpose, any suitable network connection may be employed. Presently preferred network configurations include both proprietary or dedicated networks, as well as open networks, such as the Internet. Data may be exchanged between the diagnostic systems, field service units, and remote service facility 1022 in any suitable format, such as in accordance with the Internet Protocol (IP), the Transmission Control Protocol (TCP), or other known protocols. Moreover, certain of the data may be transmitted or formatted via markup languages such as the HyperText Markup Language (HTML), or other standard languages. The presently preferred interface structures and communications components are described in greater detail below.

Within service facility 1022, messages, service requests and data are received by communication components as indicated generally at reference numeral 1082. Components 1082 transmit the service data to a service center processing system, represented generally at reference numeral 1084 in FIG. 4. The processing system manages the receipt, handling and transmission of service data to and from the service facility. In general, processing system 1084 may include one or a plurality of computers, as well as dedicated hardware or software servers for processing the various service requests and for receiving and transmitting the service data as described more fully below.

Service facility 1022 also includes a bank of operator workstations 1086 which may be staffed by personnel who address the service requests and provide off and on-line service to the diagnostic systems in response to the service requests. Also, processing system 1084 may be linked to a system of databases or other processing systems 1088 at or remote from the service facility 1022. Such databases and processing systems may include extensive database information on operating parameters, service histories, and so forth, both for particular subscribing scanners, as well as for extended populations of diagnostic equipment.

Figure 5:
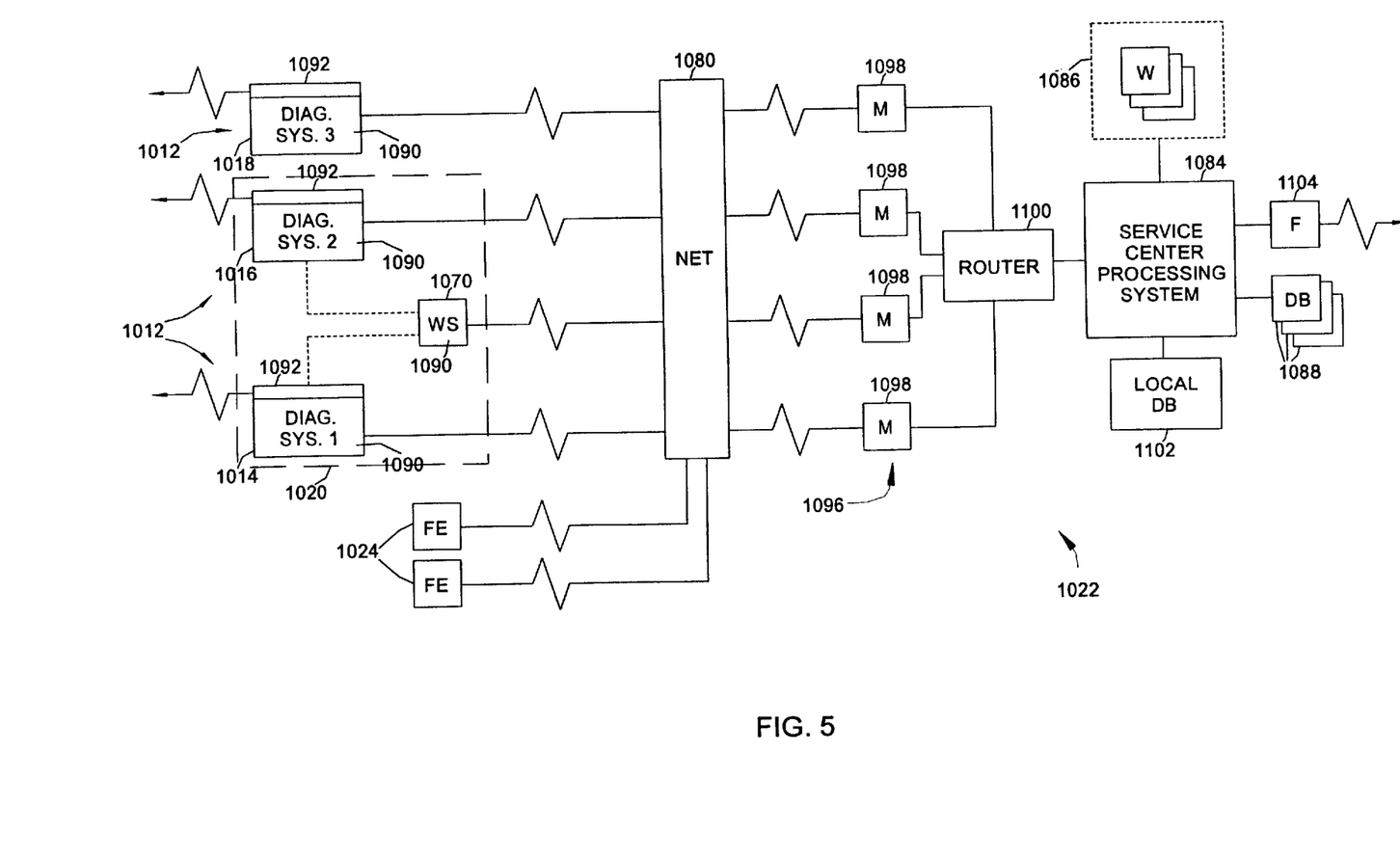
FIG. 5 is a block diagram of the systems shown in FIG. 4 illustrating certain functional components of the diagnostic systems and the service facility.

FIG. 5 is a block diagram illustrating the foregoing system components in a functional view. As shown in FIG. 5, the field service units 1024 and the diagnostic systems 1012 can be linked to the service facility 1022 via a network connection as illustrated generally at reference numeral 1080. Within each diagnostic system 1012, a uniform service platform 1090 is provided.

Platform 1090, which is described in greater detail below with particular reference to FIG. 6, includes hardware, firmware, and software components adapted for composing service requests, transmitting and receiving service data, establishing network connections and managing financial or subscriber arrangements between diagnostic systems and the service facility. Moreover, the platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access image, log and similar files needed for rendering requested or subscribed services. Where a management station 1070 is provided, a similar uniform platform is preferably loaded on the management station to facilitate direct interfacing between the management station and the service facility. In addition to the uniform service platform 1090, each diagnostic system is preferably provided with an alternative communications module 1092, such as a facsimile transmission module for sending and receiving facsimile messages between the scanner and remote service facilities.

Messages and data transmitted between the diagnostic systems and the service facility traverse a security barrier or "firewall" contained within processing system 1084 as discussed below, which prevents unauthorized access to the service facility in a manner generally known in the art. A modem rack 1096, including a series of modems 1098, receives the incoming data, and transmits outgoing data through a router 1100 which manages data traffic between the modems and the service center processing system 1084.

In the diagram of FIG. 5, operator workstations 1086 are coupled to the processing system, as are remote databases or computers 1088. In addition, at least one local service database 1102 is provided for verifying license and contract arrangements, storing service record files, log files, and so forth. Moreover, one or more communication modules 1104 are linked to processing system 1084 to send and receive facsimile transmissions between the service facility and the diagnostic systems or field service units.

Figure 6:
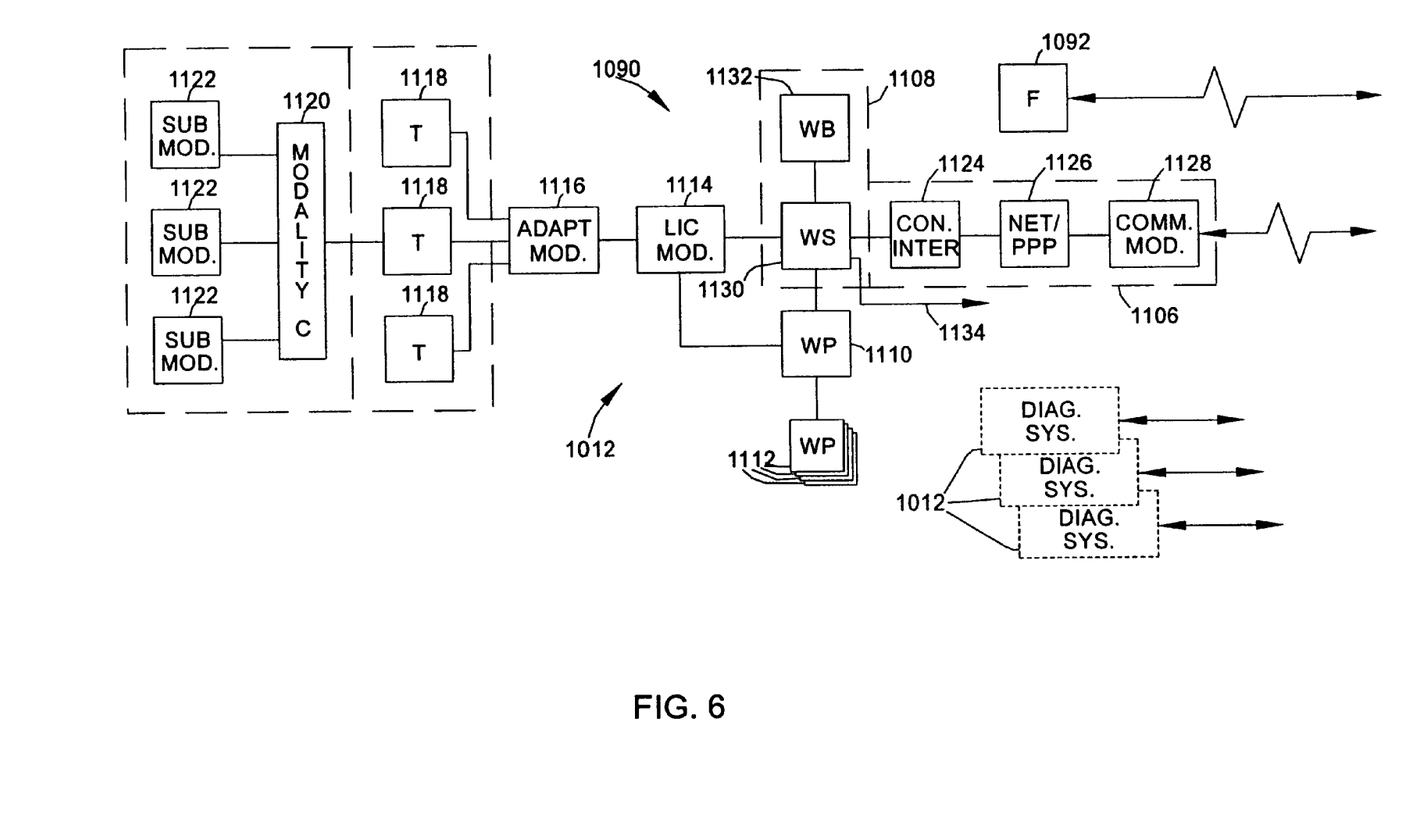
FIG. 6 is a block diagram of certain functional components within a diagnostic system of the type shown in FIG. 4 and FIG. 5 for facilitating interactive remote servicing of the diagnostic system.

FIG. 6 illustrates diagrammatically the various functional components comprising the uniform service platform 1090 within each diagnostic system 1012. As shown in FIG. 6, the uniform platform includes a device connectivity module 1106, as well as a network connectivity module 1108. Network connectivity module 1108 accesses a main web page 1110 which, as mentioned above, is preferably a markup language page, such as an HTML page displayed for the system user on a monitor at the diagnostic system. Main web page 1110 is preferably accessible from a normal operating page in which the user will configure examination requests, view the results of examinations, and so forth such as via an on-screen icon. Through main web page 1110, a series of additional web pages 1112 are accessible. Such web pages permit remote service requests to be composed and transmitted to the remote service facility, and facilitate the exchange of other messages, reports, software, protocols, and so forth as described more fully below.

It should be noted that as used herein the term "page" includes a user interface screen or similar arrangement which can be viewed by a user of the diagnostic system, such as screens providing graphical or textual representations of data, messages, reports and so forth. Moreover, such pages may be defined by a markup language or a programming language such as Java, perl, java script, or any other suitable language.

Network connectivity module 1108 is coupled to a license module 1114 for verifying the status of license, fee or contractual subscriptions between the diagnostic system and the service facility. As used herein, the term "subscription" should be understood to include various arrangements, contractual, commercial or otherwise for the provision of services, information, software, and the like, both accompanies with or without payment of a fee. Moreover, the particular arrangements manages by systems as described below may include several different types of subscriptions, including time-expiring arrangements, one-time fee arrangements, and so-called "pay per use" arrangements, to mention but a few.

License module 1114 is, in turn, coupled to one or more adapter utilities 1116 for interfacing the browser, server, and communications components with modality interface tools 1118. In a presently preferred configuration, several such interface tools are provided for exchanging data between the system scanner and the service platform. For example, modality interface tools 1118 may include applets or servlets for building modality-specific applications, as well as configuration templates, graphical user interface customization code, and so forth. Adapters 1116 may interact with such components, or directly with a modality controller 1120 which is coupled to modality-specific subcomponents 1122.

The modality controller 1120 and modality-specific subcomponents 1122 will typically include a preconfigured processor or computer for executing examinations, and memory circuitry for storing image data files, log files, error files, and so forth. Adapter 1116 may interface with such circuitry to convert the stored data to and from desired protocols, such as between the HyperText Transfer Protocol (HTTP) and DICOM, a medical imaging standard for data presentation. Moreover, transfer of files and data as described below may be performed via any suitable protocol, such as a file transfer protocol (FTP) or other network protocol.

In the illustrated embodiment, device connectivity module 1106 includes several components for providing data exchange between the diagnostic system and the remote service facility. In particular, a connectivity service module 1124 provides for interfacing with network connectivity module 1108. A Point-to-Point Protocol (PPP) module 1126 is also provided for transmitting Internet Protocol (IP) packets over remote communication connections. Finally, a modem 1128 is provided for receiving and transmitting data between the diagnostic system and the remote service facility. As will be appreciated by those skilled in the art, various other network protocols and components may be employed within device connectivity module 1106 for facilitating such data exchange.

Network connectivity module 1108 preferably includes a server 1130 and a browser 1132. Server 1130 facilitates data exchange between the diagnostic system and the service facility, and permits a series of web pages 1110 and 1112 to be viewed via browser 1132. In a presently preferred embodiment, server 1130 and browser 1132 support HTTP applications and the browser supports java applications. Other servers and browsers, or similar software packages may, of course, be employed for exchanging data, service requests, messages, and software between the diagnostic system, the operator and the remote service facility. Finally, a direct network connection 1134 may be provided between server 1130 and an operator workstation, such as management station 1070 within the medical facility (see FIGS. 4 and 5).

In a present embodiment, the components comprising network connectivity module may be configured via an application stored as part of the uniform platform. In particular, a Java application licensed to a service engineer enables the engineer to configure the device connectivity at the diagnostic system to permit it to connect with the service facility.

Figure 7:
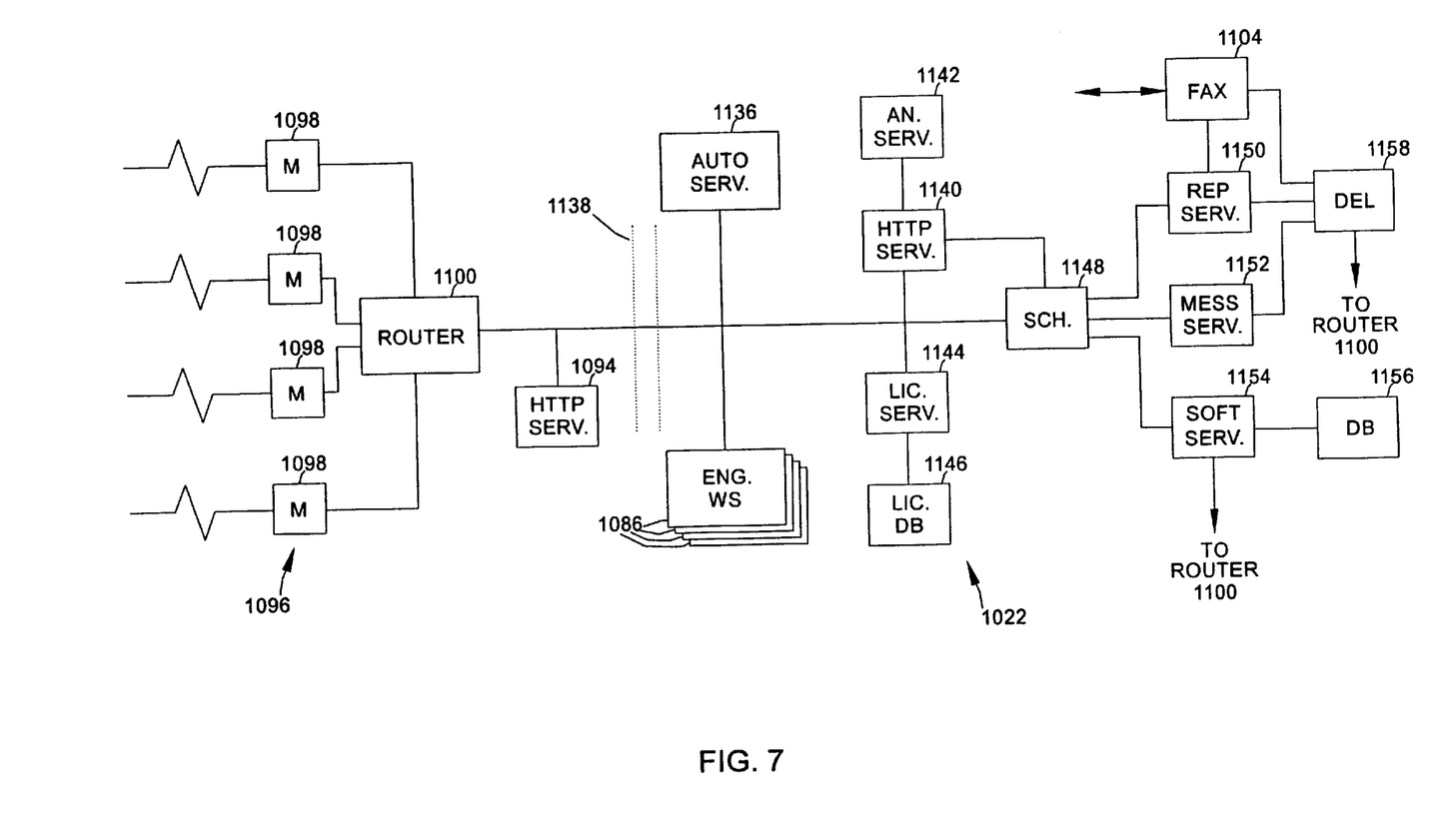
FIG. 7 is a block diagram of certain of the functional components of the service facility illustrated in FIG. 4 and FIG. 5 for rendering interactive remote service to a plurality of medical diagnostic systems.

FIG. 7 illustrates exemplary functional components for service facility 1022. As indicated above, service facility 1022 includes a modem rack 1096 comprising a plurality of modems 1098 coupled to a router 1100 for coordinating data communications with the service facility. An HTTP service server 1094 receives and directs incoming and outgoing transactions with the facility. Server 1094 is coupled to the other components of the facility through a firewall 1138 for system security. Operator workstations 1086 are coupled to the port manager for handling service requests and transmitting messages and reports in response to such requests.

An automated service unit 1136 may also be included in the service facility for automatically responding to certain service requests, sweeping subscribing diagnostic systems for operational parameter data, and so forth, as described below. In a presently preferred embodiment, the automated service unit may operate independently of or in conjunction with the interactive service components comprising processing system 1084. It should be noted that other network or communications schemes may be provided for enabling the service facility to communicate and exchange data and messages with diagnostic systems and remote service units, such as systems including outside Internet service providers (ISP's), virtual private networks (VPN's) and so forth.

Behind firewall 1138, an HTTP application server 1140 coordinates handling of service requests, messaging, reporting, software transfers and so forth. Other servers may be coupled to HTTP server 1140, such as service analysis servers 1142 configured to address specific types of service requests, as described more fully below. In the illustrated embodiment, processing system 1084 also includes a license server 1144 which is coupled to a license database 1146 for storing, updating and verifying the status of diagnostic system service subscriptions. Alternatively, where desired, license server 1144 may be placed outside of fire wall 1138 to verify subscription status prior to admission to the service facility.

Handling of service requests, messaging, and reporting is further coordinated by a scheduler module 1148 coupled to HTTP server 1140. Scheduler module 1148 coordinates activities of other servers comprising the processing system, such as a report server 1150, a message server 1152, and a software download server 1154. As will be appreciated by those skilled in the art, servers 1150, 1152 and 1154 are coupled to memory devices (not shown) for storing data such as addresses, log files, message and report files, applications software, and so forth. In particular, as illustrated in FIG. 7, software server 1154 is coupled via one or more data channels to a storage device 1156 for containing transmittable software packages which may be sent directly to the diagnostic systems, accessed by the diagnostic systems, or supplied on pay-per-use or purchase basis. Message and report servers 1152 and 1150 are further coupled, along with communications module 1104, to a delivery handling module 1158, which is configured to receive outgoing messages, insure proper connectivity with diagnostic systems, and coordinate transmission of the messages.

In a presently preferred embodiment, the foregoing functional circuitry may be configured as hardware, firmware, or software on any appropriate computer platform. For example, the functional circuitry of the diagnostic systems may be programmed as appropriate code in a personnel computer or workstation either incorporated entirely in or added to the system scanner. The functional circuitry of the service facility may include additional personal computers or workstations, in addition to a main frame computer in which one or more of the servers, the scheduler, and so forth, are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of remote service data between the diagnostic systems and a remote service facility, which is preferably implemented in an interactive manner to provide regular updates to the diagnostic systems of service activities.

As described above, both the diagnostic systems and the field service units preferably facilitate interfacing between a variety of diagnostic system modalities and the remote service facility via a series of interactive user-viewable pages. Exemplary pages include capabilities of providing interactive information, composing service requests, selecting and transferring messages, reports and diagnostic system software, and so forth. Pages facilitate the interaction and use of remote services, such as, remote monitoring, remote system control, immediate file access from remote locations, remote file storage and archiving, remote resource pooling, remote recording, and remote high speed computations.

The user can access specific documents described in text areas of the pages by selection of all or a portion of the text describing the documents. In the presently preferred embodiment, the accessed documents may be stored in local memory devices within the diagnostic system, or selection of the text may result in loading of a uniform resource locator (URL) for accessing a remote computer or server via a network link.

Advantageously, service system 1010 (FIG. 4) provides remote services, such as, remote upgrades, remote diagnostics, remote servicing, remote viewing, remote file storage, remote control, and remote adjustments to the reformatting and reconstruction methods, parameters, or functions. Furthermore, remote services may provide for contractual arrangements, such as, per use licenses which lease the medical diagnostic equipment based on use. Additionally, remote services may also include expert on-line assistance for image scanning techniques, image analysis, pathology detection, imaging unit maintenance, and other expert-aided operations.

While the embodiments illustrated in the Figures and described above are presently preferred, it should be understood that the embodiments are offered by way of example only. Other embodiments may include enhanced remote features made possible by the network structures and functionalities described herein. The invention is not limited to a particular embodiment, but extends to various modifications, combinations, and permutations that nevertheless fall within the scope and spirit of the appended claims.

What is claimed is:

1. A computed tomography system comprising an x-ray source, an x-ray detector aligned with the x-ray source, a processor coupled to the x-ray detector, and a display for displaying reconstructed images, the processor programmed to perform at least one of:
   generating a partially reconstructed image for display on the display;
   dynamically reformatting images for display on the display; and
   communicating the partially reconstructed image, the reformatted images, or data associated with the system to a remote facility, the remote facility providing remote services.

2. A computed tomography system in accordance with claim 1 wherein to generate the partially reconstructed image, the processor is configured to weight data to provide a smooth transition from a first image to a next image.

3. A computed tomography system in accordance with claim 2 wherein the processor overscan weights the data.

4. A computed tomography system in accordance with claim 1 wherein the image reformation is performed utilizing image interpolation.

5. A computed tomography system in accordance with claim 1 further comprising a suspension system for suspending the display from a ceiling.

6. A computed tomography system in accordance with claim 1 wherein the display further comprises a user interface comprising an indicator for indicating x-ray exposure.

7. A computed tomography system in accordance with claim 6 wherein the indicator indicates at least one of x-ray exposure within a burst and x-ray exposure accumulated from multiple bursts.

8. A computed tomography system in accordance with claim 1 wherein the display comprises image controls, a messages section, and display controls.

9. A computed tomography system in accordance with claim 8 wherein the display is controllable remotely.

10. A computed tomography system in accordance with claim 1 wherein the processor is further configured to magnify images for display.

11. A computed tomography system in accordance with claim 10 wherein to magnify the images, the processor executes at least one of (a) a two pass algorithm in which each of the passes represents interpolation in the x and y directions respectively, and (b) a bilinear interpolation algorithm including a two dimensional convolution filter.

12. A computed tomography system in accordance with claim 1 wherein the display is a wide angle flat panel display.

13. A computed tomography system comprising an x-ray source, an x-ray detector aligned with the x-ray source, a processor coupled to the x-ray detector, and a display for displaying reconstructed images, the processor configured to generate a partially reconstructed image for display on the display, to weight data to provide a smooth transition from a first image to a next image, and to communicate the partially reconstructed image or data associated with the system to a remote facility, the remote facility providing remote services.

14. A computed tomography system in accordance with claim 13 wherein the processor is further configured to dynamically reformat images for display on the display wherein the image reformation is performed utilizing image interpolation.

15. A computed tomography system in accordance with claim 13 wherein the processor is further configured to magnify images for display, and wherein to magnify the images, the processor executes at least one of (a) a two pass algorithm in which each of the passes represents interpolation in the x and y directions respectively, and (b) a bilinear interpolation algorithm including a two dimensional convolution filter.

16. A computed tomography system comprising an x-ray source, an x-ray detector aligned with the x-ray source, a processor coupled to the x-ray detector, and a display for displaying reconstructed images, the processor configured to dynamically reformat images for display on the display and to communicate the reformatted images or data associated with the system to a remote facility, the remote facility providing remote services.

17. A computed tomography system in accordance with claim 16 wherein the processor overscan weights the data.

18. A computed tomography system in accordance with claim 16 wherein the processor is further configured to generate a partially reconstructed image for display on the display, and to weight data to provide a smooth transition from a first image to a next image.

19. A computed tomography system in accordance with claim 18 wherein the image reformation is performed utilizing image interpolation.

20. A computed tomography system in accordance with claim 19 wherein a plane for the image reformation can be specified at any arbitrary angle.

21. A computed tomography system in accordance with claim 16 wherein the processor is further configured to magnify images for display.

22. A computed tomography system in accordance with claim 21 wherein to magnify the images, the processor executes at least one of (a) a two pass algorithm in which each of the passes represents interpolation in the x and y directions respectively, and (b) a bilinear interpolation algorithm including a two dimensional convolution filter.

* * * * *